(12) United States Patent
Sabczynski et al.

(10) Patent No.: US 12,369,893 B2
(45) Date of Patent: Jul. 29, 2025

(54) METHOD FOR USE IN ULTRASOUND IMAGING

(71) Applicant: KONINKLIJKE PHILIPS N.V., Eindhoven (NL)

(72) Inventors: Jörg Sabczynski, Norderstedt (DE); Cornelis Petrus Hendriks, Eindhoven (NL); Rafael Wiemker, Kisdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 117 days.

(21) Appl. No.: 18/282,571

(22) PCT Filed: Mar. 14, 2022

(86) PCT No.: PCT/EP2022/056422
§ 371 (c)(1),
(2) Date: Sep. 18, 2023

(87) PCT Pub. No.: WO2022/200084
PCT Pub. Date: Sep. 29, 2022

(65) Prior Publication Data
US 2024/0180529 A1  Jun. 6, 2024

(30) Foreign Application Priority Data
Mar. 22, 2021 (EP) .................... 21164045

(51) Int. Cl.
*A61B 8/00* (2006.01)

(52) U.S. Cl.
CPC .......... *A61B 8/5269* (2013.01); *A61B 8/4245* (2013.01); *A61B 8/465* (2013.01); *A61B 8/5238* (2013.01)

(58) Field of Classification Search
CPC ..... A61B 8/5269; A61B 8/4245; A61B 8/465; A61B 8/5238
See application file for complete search history.

(56) References Cited

U.S. PATENT DOCUMENTS

| | | |
|---|---|---|
| 2010/0179428 A1 | 7/2010 | Pedersen et al. |
| 2014/0200440 A1 | 7/2014 | Iannotti et al. |
| 2016/0048958 A1 | 2/2016 | Miga et al. |

(Continued)

FOREIGN PATENT DOCUMENTS

EP    3669758 A1    6/2020

OTHER PUBLICATIONS

International Search Report and Written Opinion for PCT/EP2022/056422; Mailing date May 9, 2022, 10 pages.

(Continued)

*Primary Examiner* — Dixomara Vargas (57) ABSTRACT

A method is provided for recording or representing captured ultrasound-derived information. The method is based on obtaining positioning information related to an ultrasound probe during execution of an ultrasound examination, and using this to associate captured data samples, or information derived therefrom, with anatomical position information for the data samples. The link between the two is achieved using an anatomical model which can relate probe surface position with anatomical body structure underlying the surface. A map can be generated of the obtained data as a function of position across the surface of the anatomical body. i.e. effectively a projection of the data onto the object 2D surface.

15 Claims, 5 Drawing Sheets

(56) References Cited

U.S. PATENT DOCUMENTS

| | | |
|---|---|---|
| 2019/0251327 A1 | 8/2019 | LaViola et al. |
| 2020/0046314 A1 | 2/2020 | Neben et al. |
| 2020/0178774 A1 | 6/2020 | Komp |

OTHER PUBLICATIONS

Goffi, A. et al., "The sound of air: point-of-care lung ultrasound in perioperative medicine", Can J Anesth/J Can Anesth, 2018, vol. 65, pp. 399-416.

Baloescu, C. et al., "Automated Lung Ultrasound B-Line Assessment Using a Deep Learning Algorithm", IEEE Transactions on Ultrasonics, Ferroelectrics, and Frequency Control, 2020, vol. 67, No. 11, pp. 2312-2320.

Cadena, C. et al., "Past, Present, and Future of Simultaneous Localization and Mapping: Toward the Robust-Perception Age", IEEE Transactions on Robotics, 2016, vol. 32, No. 6, pp. 1309-1332.

Blaffert, T. et al., "Lung lobe modeling and segmentation with individualized surface meshes", Proceedings of SPIE 6914, Medical Imaging 2008: Image Processing, 691411-1, 10 pages.

Anonymous, "Simultaneous localization and mapping", Wikipedia, 2023, retrieved from: https://en.wikipedia.org/wiki/Simultaneous_localization_and_mapping, 10 pages.

METHOD FOR USE IN ULTRASOUND IMAGING

CROSS-REFERENCE TO PRIOR APPLICATIONS

This application is the U.S. National Phase application under 35 U.S.C. § 371 of International Application No. PCT/EP2022/056422, filed on Mar. 14, 2022, which claims the benefit European Patent Application No. 21164045.3, filed on Mar. 22, 2021. These applications are hereby incorporated by reference herein.

FIELD OF THE INVENTION

The invention relates to the field of ultrasound imaging.

BACKGROUND OF THE INVENTION

Within the domain of ultrasound examination, there are many types of measurement information or other secondary information which can be derived during a scan but which are not directly visually representable in a spatial format. For example, there are many ultrasound-derived parameters or features which are an indirect feature of the acquired ultrasound data sample itself, rather than an intrinsic feature of the anatomy presented in the ultrasound data. For this reason, deriving this information requires highly skilled practitioners, and is difficult to record in a standardized way that enables interpretation and understanding by less skilled practitioners.

One example is ultrasound scanning of the lungs, and the detection of B-lines. A-lines and lung sliding. These are artefacts of the ultrasound image data itself.

Furthermore, situations may arise in which an experienced sonographer may not be available to perform the examination, and it must therefore be performed at the point of care by a less experienced person or even a novice. Here, again, a means for recording the examination data in a standardized way that allows it to be reviewed later by a more experienced sonographer would be of benefit.

One domain where ultrasound scanning by less experienced personnel has been a common phenomenon is in the context of assessment of the lungs of COVID-19 patients.

Lung ultrasound is increasingly being used at the point-of-care (point-of-care ultrasound, POCUS). Since it is a fast and easy bedside test, and with equipment which is easy to disinfect, it has also had widespread use for the assessment of COVID-19 patients. A severe problem for the management of critically ill COVID-19 patient is the high risk of infection. In the context of ultrasound, this leads to several workflow constraints, which cannot be solved by distance measures because of the contact nature of ultrasound.

Any person working with an infected patient needs to put on personal protective equipment (PPE) consisting of gloves, face mask, protective glasses, and protective clothing, which is very time consuming. Furthermore, an experienced sonographer is often not available at the bedside, for example due to: access to an infected patient being restricted to the immediate care team in order to reduce the infection risk; an absence of trained lung sonographers in rural community health centers; and a shortage of PPE in a hospital leading to limitations on the number of care givers being able to enter the patient room.

Consequently, in the assessment and triage of COVID-19 patients, many situations are possible in which a lung ultrasound examination will be performed by an inexperienced person instead of an experienced sonographer at the point-of-care, following which an experienced sonographer needs to judge if the examination was performed optimally before basing clinical decisions on its results. Lung ultrasound often relies not only on direct tissue visualization as in other organs but on the interpretation of imaging artefacts. The reason is that the ultrasound beam is blocked by air due to the difference in acoustic impedance between lung and other tissues and therefore visualization of healthy, air filled lung tissue is difficult. Nevertheless, image artefacts can be used to distinguish healthy lung tissue from diseased lung tissue. Some image artefacts are even characteristic for certain tissue changes.

There is a need for an improved means of acquiring, recording and presenting ultrasound-derived measurement data of a type which is not inherently spatially presented in the native ultrasound data, and which pertains to features or artefacts of the data itself.

SUMMARY OF THE INVENTION

The invention is defined by the claims.

According to examples in accordance with an aspect of the invention, there is provided a computer-implemented method for use in ultrasound examination of an internal anatomical object of a subject, comprising: receiving ultrasound data comprising a series of data samples acquired from an ultrasound probe moved over a surface of a body of the subject during a first period: applying a pre-determined processing operation to derive from the ultrasound data samples secondary data relating to features and/or artefacts detectable in at least a subset of the ultrasound data samples: receiving tracking data representative of movement of the ultrasound probe over the body surface during the course of the examination period: accessing an anatomical model, the model including a representation of (i) the anatomical object of interest and (ii) a surface of the body overlying the anatomical object of interest, and (iii) a spatial relationship between the anatomical object and the surface of the body: determining, based on the tracking data, a probe position on the subject body surface as a function of time: and generating a surface map comprising a projection of the secondary data values onto a surface of the anatomical object, the projection based on the probe position as a function of time, and based on the anatomical model.

Embodiments of the present invention are based on tracking in real time the position of an ultrasound probe on a subject's skin during a scan, and then using an anatomical model of the subject's anatomy to permit a spatial registration of secondary data extracted from the ultrasound data with a surface of an underlying anatomical object. In other words, embodiments are based on simultaneously acquiring two data streams: one representative of the secondary data values (derived from the ultrasound data) and one representative of the position data of the probe. The model is then used to marry or correlate the two, so that each secondary data value or measurement can be associated with a known position on a surface of the anatomy to which that value corresponds.

The model hence permits a spatial registration or mapping function between a detectable probe location on the subject's body (e.g. chest) and a corresponding location on a surface of the underlying anatomy (e.g. lung) to which the secondary data acquired at that body surface position corresponds.

The model may be a personalized model. i.e. personalized to the subject. This makes the spatial correspondence between the secondary data and the anatomical object surface more accurate. The surface map is simply a data representation of the secondary data values as a function of corresponding location on the modelled anatomical object surface. It can optionally be represented in a visual form in addition.

The model preferably has a co-ordinate system relative to which points of the subject body surface are defined, and relative to which camera position and transducer position can be determined.

The method may comprise a step of identifying for each ultrasound data sample a corresponding probe position at which the sample was acquired.

The method may comprise determining, based on the determined probe positions for each ultrasound data sample, and the anatomical model, a spatial registration between the secondary data and locations across a surface of the anatomical object of interest.

The secondary data may comprise a respective secondary data sample for each ultrasound data sample, and wherein the method comprises determining for each secondary data sample a location on a surface of the anatomical object to which the secondary data sample corresponds based on the determined probe position for the sample, and based upon the anatomical model.

The generating of the surface map can optionally be done in real time with acquisition of the ultrasound and tracking data, or it can be done offline, based on ultrasound and tracking data streams which have been previously acquired and recorded for later recall.

The method may further comprise generating a data output representative of the generated surface map. The method may comprise communicating the generated surface map to an external processor, computer, and/or a display device.

The method may further comprise a step of registering the co-ordinate system of the tracking data to a co-ordinate system of the anatomical model.

In some embodiments, the tracking data may be camera image data representative of the movement of the probe over the body surface. The camera image data may be 3D camera data. Alternatives to camera image data may include for example electromagnetic tracking means, mechanical arms with trackable pose, acoustic tracking means (e.g. sonar-like localizers) or any other suitable positioning apparatus.

In some embodiments, determining the probe position may be based on registering surface landmarks detectable in the image data with the subject body surface landmarks in the anatomical model. This provides a mechanism for directly registering the native co-ordinate system of the camera image tracking system with the anatomical model co-ordinate system. As an alternative, a tracking processor might be provided, arranged to receive the camera image data and adapted to output a position co-ordinate of the probe within a camera field-of-view (FOV) co-ordinate system (as a function of time). The resulting position co-ordinates of the probe may then need to be transformed into co-ordinates within the co-ordinate system of the subject body, e.g, the co-ordinate system of the anatomical model. This may require a pre-calibration step between the camera co-ordinate system and the model co-ordinate system. In some embodiments, the method may further comprise receiving an indication of a position of the camera relative to the subject. This may be manually entered by a user or the method may comprise determining the position of the camera relative to the subject based on the image data captured by the camera. More generally the function of this step is to determine a spatial relation between the co-ordinate system of the camera image frame used to track the probe and co-ordinate system of the subject anatomical model.

In some embodiments, the method may further comprise generating a visual representation of the surface map comprising a visual projection of the secondary data onto a surface of the modelled anatomical object.

In some embodiments, the ultrasound data samples may be ultrasound image frames, and the secondary data may relate to presence of pre-determined types of image features and/or image artefacts within each image frame.

In some embodiments, the anatomical model may define a model co-ordinate system, and wherein the probe position may be determined relative to the model co-ordinate system.

In some embodiments, the ultrasound data may be received in real time with the data acquisition by the probe, and wherein receiving the camera image data and the determining the probe position may be performed in real time with the receipt of the ultrasound data.

In some embodiments, the generating of the surface map may be performed in real time with the ultrasound data acquisition and with the determination of the probe position, and the method may further comprise generating in real time a visual representation of the surface map, comprising a visual projection of the secondary data onto a surface of the modelled anatomical object. The real-time generated surface map may be displayed on a display device so that an operator can observe progress of the examination.

In some embodiments, the method may further comprise accessing a predetermined scan protocol including a series of target positions for the ultrasound scanner during the examination period, and generating a display output for presentation on a display device representative of the target probe positions of the scan protocol superimposed upon an image representation of the subject body surface. The image representation may be provided by real time camera image data in the case that the tracking data is camera image data, or may be a graphical representation of the body surface, e.g. a model representation of the body surface. If performed in real-time, this display output effectively provides an augmented reality image representation of the subject body surface, augmented with the target probe positions.

In some embodiments, the method may comprise a step of personalizing the accessed anatomical model for the subject, where the personalizing may comprise fitting one or more adjustable fitting parameters of the model to the subject based on acquired camera image data of the subject, ultrasound data of the subject, and/or measurement or personal characteristics data of the subject. The measurement data may include standard measurements of the subject, e.g. height, weight, chest and waist circumference. Personal characteristics data may include for example age, gender, ethnicity, relevant medical history.

This step may be done in real time with the generating of the surface map. Where the tracking data is camera image data, the fitting may be based on identifying one or more body surface visual landmarks comprised by the initial model in the one or more camera image frames: and fitting the parameters of the initial model to the subject body surface based on the landmarks to derive the subject model.

In some embodiments, the anatomical model is a personalized anatomical model for the subject.

The method may further comprise a preliminary setup phase for configuring the personalized anatomical model, the setup phase performed in advance of receiving the ultrasound data, and comprising: retrieving an initial version of the anatomical model, and wherein the model includes a plurality of adjustable fitting parameters: acquiring one or more camera image frames of the subject body surface: identifying one or more body surface visual landmarks comprised by the model in the one or more camera image frames: and fitting the parameters of the initial model to the subject body surface based on the landmarks to derive the personalized subject model. In this set of embodiments, the personalizing of the anatomical model may be done as a preliminary step. Additional or alternatively, the model may be personalized to the subject in advance of the method beginning, based on personal medical image data for the subject, e.g. based on CT scan data. In this way, once the method starts, the accessed anatomical model is already personalized to the subject anatomy.

In some embodiments, the method may comprise processing the camera image data to automatically detect the surface landmarks.

In some embodiments, the method may comprise receiving user input data indicative of a user-indicated position of one or more of the surface landmarks on one or more image frames of the camera image data.

In some embodiments, the anatomical object of interest may comprise at least a portion of the lungs of the subject.

In some embodiments, the secondary data may comprise a representation of presence of one or more of: lung sliding artefacts. A-line artefacts, and B-line artefacts. It may comprise a direct or indirect representation. It may comprise a representation which is indirectly indicative of one or more of these phenomena for example.

According to another aspect of the invention, there is provided a computer program product comprising code means configured, when executed on a processor, to cause the processor to perform a method in accordance with any in accordance with any example or embodiment outlined above or described below, or in accordance with any claim of this application.

According to another aspect of the invention, there is provided a processing arrangement comprising: an input/output: and one or more processors adapted to: receive at the input/output ultrasound data comprising a series of data samples acquired from an ultrasound probe moved over a surface of a body of the subject during an examination period: apply a pre-determined processing operation to derive from the ultrasound data samples secondary data relating to features and/or artefacts detectable in at least a subset of the ultrasound data samples: receive at the input/output tracking data representative of the movement of the ultrasound probe over the body surface during the course of the 20) examination period: access an anatomical model, the model including a representation of (i) the anatomical object of interest and (ii) a surface of the body overlying the anatomical object of interest, and (iii) a spatial relationship between the anatomical object and the surface of the body: determine, based on the tracking data, a probe position on the subject body surface as a function of time: and generate a surface map representative of a projection of the secondary data values onto a surface of the anatomical object, the projection based on the probe position as a function of time, and based on the anatomical model.

According to another aspect of the invention, there is provided a system, comprising: an ultrasound sensing apparatus including an ultrasound probe: a tracking apparatus for acquiring tracking data of the ultrasound probe during the course of the examination period: and a processing arrangement in accordance with any example or embodiment outlined above or described below, or in accordance with any claim of this application, the input/output of the processing arrangement communicatively coupled with the tracking apparatus and the ultrasound sensing apparatus for receiving the tracking data and the ultrasound data respectively. The tracking apparatus may comprise a camera for imaging the body surface during the course of the examination period, and wherein the tracking data is camera image data.

In some embodiments, the system may further comprise a user interface for displaying a visual representation of the generated surface map, and optionally wherein the user interface is further adapted to permit annotation by a user of locations of one or more surface visual landmarks in each of one or more image frames from the camera image data. The surface visual landmarks may be comprised by the model.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention relates to a method for recording or representing captured ultrasound-derived information in a way that spatially relates it to the anatomy to which it corresponds. The method is based on obtaining positioning information related to an ultrasound probe during execution of an ultrasound examination, and using this to associate captured data samples, or information derived therefrom, with anatomical position information for the data samples. The link between the two is achieved using an anatomical model which can relate probe surface position with anatomical body structure underlying the surface. A map can be generated of the obtained data as a function of position across the surface of the anatomical body. i.e. effectively a projection of the data onto the object 2D surface.

Embodiments of the invention thereby provide a method for ultrasound imaging of a subject such that, even if the imaging were carried out by an inexperienced sonographer, the results would be of sufficient quality to be clinically acceptable. The method allows for an ultrasound probe to be passed over the surface of the body of a subject to capture ultrasound data while tracking the probe using, for example, a camera, for example a camera of a smartphone or tablet. Reasons for an inexperienced sonographer obtaining results of insufficient quality may be, for example, failing to interpret secondary information from the ultrasound data correctly. In the case that camera tracking is used, image processing may for example be used to identify a probe position, relative to a defined co-ordinate system. From this information, the position of the probe can be related to a representation of a generic or personalized body model (i.e. an anatomical model) and the captured ultrasound data can then be processed in such a way that the data, too, is related to the representation of the body. Thus, a model of the target internal organ/object can be overlaid with data derived from the ultrasound scanning (e.g. secondary ultrasound data) and presented to an experienced sonographer for clinical use.

Figure 1:
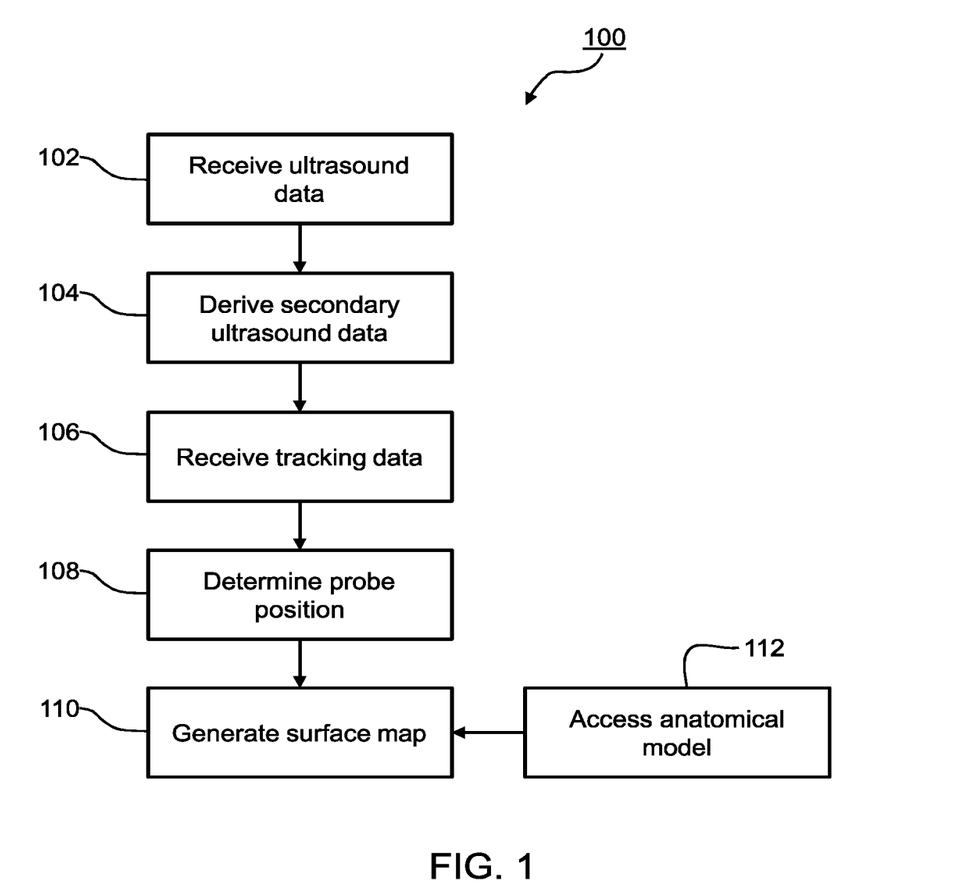
FIG. 1 is a flow diagram of a computer-implemented method for use in ultrasound examination of an internal anatomical object of a subject.

Referring to FIG. 1, there is depicted a flow diagram of a computer-implemented method 100 in accordance with one or more embodiments, for use in ultrasound examination of an internal anatomical object of a subject 208. In summary, the method 100 comprises steps of: receiving 102 ultrasound data, deriving 104 secondary ultrasound data, receiving 106 tracking data, accessing 112 an anatomical model, determining 108 a probe position, and generating 110 a surface map of the secondary data.

An aspect of the invention provides the method. A further aspect of the invention may provide a computer or a processing arrangement configured to carry out the computer-implemented method. A further aspect of the invention may provide a computer program product comprising code means configured, when executed on a processor, to cause the processor to perform the method.

Receiving 102 the ultrasound data comprises receiving a series of data samples acquired from an ultrasound probe moved over a surface of a body of the subject during a first period. The first period may correspond to an examination period.

The ultrasound probe may be any device that is able to emit ultrasound frequency sound waves and sense returned ultrasound echoes. The ultrasound probe comprises one or more ultrasonic transducers. The ultrasound probe may be also referred to as an ultrasound transducer unit.

By way of example, the ultrasound data samples may comprise ultrasound image frames. Alternatively, the ultrasound data samples may comprise ultrasound echo data, which may be raw echo data (i.e. RF data), or echo data which has been at least partially post-processed.

In one advantageous set of examples, the internal anatomical object of interest of a subject may comprise at least a portion of the lungs of the subject. However, this is one example only, and the general inventive concept is applicable to imaging of any internal anatomical object, e.g. any internal organ or portion of an organ.

Deriving 104 the secondary ultrasound data may comprise applying a pre-determined processing operation to derive 104 from each of the ultrasound data samples secondary data relating to features and/or artefacts detectable in each ultrasound data sample. The secondary data may relate to presence of pre-determined types of image features and/or image artefacts within each image frame. The pre-determined processing operation may comprise an automated algorithm that can be used to analyze the ultrasound data in the form of ultrasound images and detect certain image features or imaging artefacts in the ultrasound images.

By way of just one example, a deep learning algorithm may be used. By way of one example, an exemplary algorithm for performing the identification or extraction of the features or artefacts from ultrasound image data is outlined in the following paper: C. Baloescu et al., "Automated Lung Ultrasound B-Line Assessment Using a Deep Learning Algorithm." IEEE Transactions on Ultrasonics. Ferroelectrics, and Frequency Control, vol. 67, no. 11. pp. 2312-2320. November 2020.

The secondary data may comprise at least one respective secondary data sample for each ultrasound data sample. The secondary data may comprise multiple secondary datasets, wherein each secondary dataset includes a respective secondary data sample for each ultrasound data sample. The method 100 may comprise determining for each secondary data sample a location on a surface of the anatomical object to which the secondary data sample corresponds based on the determined probe position for the sample, and based upon the anatomical model.

By way of one non-limiting example, where the ultrasound data is ultrasound lung data, the secondary data may comprise a representation of presence of one or more of: lung sliding artefacts. A-line artefacts, and B-line artefacts.

Receiving 106 the tracking data comprises receiving tracking data representative of movement or position of the ultrasound probe over the body surface during the course of the examination period. The tracking data may be spatial data. It may be visualization data.

By way of example, the tracking data may be camera image data representative of the movement of the probe over the body surface during the course of the first period. In one particular set of examples, the camera image data may be obtained from a mobile device such as a phone or tablet which comprises at least one camera. The camera data may in some examples be 3D camera data (e.g. RGB-D camera data), but this is not essential. Alternatives to camera image data may include for example electromagnetic tracking means, mechanical arms with trackable pose, acoustic tracking means e.g. sonar-like localizers or any other suitable positioning apparatus.

Accessing 112 an anatomical model comprises accessing a model including a representation of the anatomical object of interest and of a surface of the subject body overlying the anatomical object of interest, and of a spatial relationship between the anatomical object and the surface of the subject body. Optionally, the model may include one or more subject body surface visual landmarks.

There are different options for the anatomical model. The anatomical model may be a generic anatomical model, or may be a personalized anatomical model. Where the model is personalized (i.e. to the anatomy of the subject), the personalization may be done in advance or may be done as part of the method. When done as part of the method, it may be done as part of a preliminary setup phase (before the ultrasound exam, extending over the first period, begins for example), or may be done in real time as ultrasound data is received. Options for personalization of the model will be explained in greater detail to follow.

Determining 108 a probe position comprises determining the position of the ultrasound probe on the surface of the body of the subject as a function of time. The determined probe position is based on the tracking data. This step effectively comprises converting the tracking data in its original raw form into a set of numerical or quantitative position indicators (e.g. values or vectors) for the probe over the course of the first period. For example, it may comprise deriving a set of vector co-ordinate positions of the probe as a function of time throughout the examination period. These may be represented in a 20) certain co-ordinate system, which may be a native co-ordinate system of the tracking system and/or may be a co-ordinate system embodied by the model.

Depending upon the tracking technology used, there are different ways to derive the position data for the probe based on the tracking data. The position may be represented in terms of a co-ordinate system of the tracking system, which is then registered for example to a co-ordinate system of the model. Alternatively, the tracking system may be pre-registered or pre-calibrated to the model co-ordinate system, so that the output of the tracking system is automatically a position of the probe within the reference frame of the model. Details will be explained further later.

Generating 110 a surface map comprises projecting the secondary data values or samples onto a modelled surface of the anatomical object, the projection based on the probe position as a function of time, and based on the anatomical model.

Each secondary data sample may be determined from a respective ultrasound data sample acquired from the ultrasound probe. The position as a function of time of the ultrasound probe on the surface of the subject's body is derived from the tracking data. Hence, the position as a function of time of each secondary data value on the surface of the body of the subject can be determined. As discussed previously, the position as a function of time of the probe in relation to the anatomical model can be determined. Since the anatomical model includes both the surface of the anatomical object of interest and the surface of the body of the subject, the position of the probe on the surface of the body of the subject can be related to the position of the probe on the surface of the anatomical object of interest. By way of non-limiting example, the relation can achieved by applying a mapping function. For example, it may be achieved by performing a vertical mapping with a vertical line drawn between each position on the surface of the body of the subject and the position on the surface of the anatomical body of interest. Hence, each secondary data value can be projected from the known position on the surface of the body of the subject to the projected position on the surface of the anatomical body of interest. In other examples, a more complex mapping function between body surface position and anatomical object surface position may be used, for instance which takes into account propagation direction of the ultrasound beams into the body from the body surface.

In advantageous examples, the method 100 may further comprise generating a visual representation of the surface map, comprising a visual projection of the secondary data onto a surface of the modelled anatomical object.

The surface maps can in general be used to assess the presence and extent of any disease and also for monitoring of disease progression over time. The automated analysis of the ultrasound images (i.e. deriving the secondary data) and the generated surface map can be used for follow-up and for comparing changes in the subject over time. In other words, the method provides a means for generating a standardized spatial representation of a particular property or pathology of a subject. Thus, the method offers the benefits of: creating representations of the spatial extent of diseases: and monitoring disease progression over time.

Figure 2:
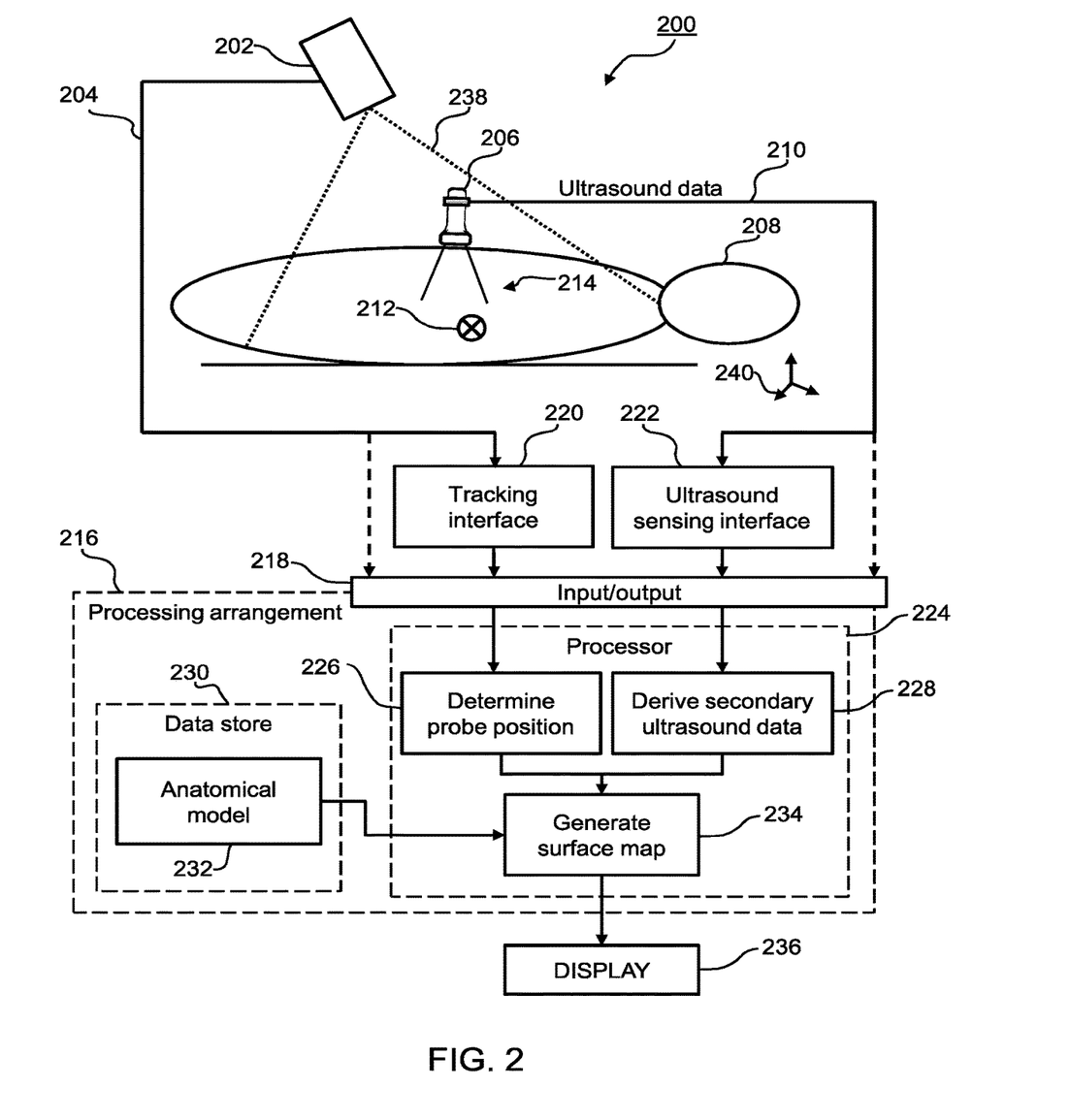
FIG. 2 is a schematic representation of ultrasound imaging of a subject, according to one or more embodiments of the invention.

Referring to FIG. 2, there is depicted an example system 200 suitable for use in acquiring the parallel ultrasound and tracking data which is used as the input data for the above-described method. The figure further illustrates an example workflow for the method, including a processing flow of acquired data. The system includes a processing arrangement 216 adapted to perform the computer-implemented method in accordance with any of the embodiments outlined in this disclosure, or in accordance with any claim of this application. One aspect of the invention may provide the processing arrangement alone. Another aspect may provide the system including a tracking apparatus and/or an ultrasound sensing apparatus.

FIG. 2 includes a schematic representation of the subject 208 undergoing ultrasound imaging of an internal anatomical object 212. This may be the lungs for example, or any other organ or anatomical body, such as the heart, liver, kidney, colon, or other soft tissue organ.

The processing arrangement 216 comprises an input/output 218 and one or more processors 224. The input/output 218 may be configured to be an interface between the data acquisition hardware of the system (e.g. tracking apparatus and ultrasound imaging apparatus) and the one or more processors of the processing arrangement.

The illustrated system 200 includes a tracking apparatus 202, 220, and an ultrasound sensing apparatus 206, 222. The tracking apparatus includes a tracking device 202 which has a spatial field of view (FOV) 238, or a spatial area of sensitivity. The tracking device may comprise one or more sensing elements. The tracking device may acquire spatial data representative of the relevant FOV 238. In some embodiments, the tracking device 202 may comprise a camera and accordingly the output of the tracking device may comprise camera image data. In other examples, the tracking device 202 may comprise another other form of spatial sensing apparatus, for instance a LIDAR sensing system, radio-frequency sensing, optical systems operating outside the visual frequency band (e.g. infrared (IR) cameras), acoustic systems (e.g. SONAR transceivers), and/or any conceivable real-time locating/tracking systems (RTLS/ RTTS). In some examples, the tracking device may be adapted to operate based on communication with a transceiver physically coupled to the ultrasound probe 206 being tracked. This may for instance be based on electromagnetic communication or acoustic communication.

The depicted system 200 further includes an ultrasound sensing apparatus, which includes an ultrasound probe 206 (or ultrasound transducer unit) operatively coupled with an ultrasound sensing interface 222. The ultrasound sensing interface may comprise one or more processors and may be adapted to receive the raw echo data 210 acquired by the ultrasound probe during operation, and perform some post processing of the data. Alternatively, the interface may pass the data unaltered directly to the input/output 218 of the processing arrangement.

In some examples, the ultrasound sensing interface 222 may comprise one or more processors adapted to derive ultrasound images from the acquired ultrasound data 210. For example it may acquire ultrasound image frames in real time with acquisition of the ultrasound data. In some examples, the data samples passed to the input/output 218 may each comprise an ultrasound image frame generated by the ultrasound sensing interface 222. Most typically, the ultrasound apparatus might be facilitated by a stand-alone diagnostic ultrasound imaging system, for example trolley mounted, which includes the ultrasound probe 206 and includes an interface 222 having one or more processors adapted to process the data. In a further example, the ultrasound imaging system may be implemented by a handheld ultrasound probe operatively coupled to a mobile computing device such as a tablet computer or smartphone.

In operation, a subject 208 upon whom an examination is to be performed, is positioned within the field of view 238 of the tracking device 202. In particular, the surface 214 of the subject body over which the ultrasound probe 206 is to be passed should be within the field of view of the tracking device.

An ultrasound examination of the internal anatomical object 212 is then performed over the course of an examination period (referred to above as the first period). Throughout the course of the examination period, the movement of the ultrasound probe 206 by an operator over the surface 214 of the body of the subject 208 is tracked by the tracking device 202. This therefore results in two temporally synchronous data streams: one being the output data 204 from the tracking device 202, and the other being the ultrasound data output 210 from the ultrasound probe 206. Each data stream may include a series or stream of data samples, each having a timestamp. The clocks or timing schemes of the tracking apparatus 202, 220 and the ultrasound sensing apparatus 210, 222 may be synchronized.

The system 200 may include a tracking interface 220 which is arranged to receive the direct output from the tracking device 202. For example, the tracking interface may convert the raw sensing data from the tracking device 202 into tracking data, for example in the form of vector positioning data of the ultrasound probe 206 within the field of view 238, for instance within a coordinate system of the tracking apparatus.

By way of example, where the tracking device 202 comprises a camera, or a mobile device comprising at least one camera, the tracking device 202 may be placed such that it points towards the surface of the subject 208. The camera may be hand held and/or the camera may not require a fixed position. The output data 204 from the camera 202 may comprise an image stream from the camera. The image stream may be analyzed by the tracking interface with a suitable method configured to extract the position of the ultrasound probe 206 relative to the subject. Computer vision methods exist for tracking the positioning of objects within camera image data, and this will be explained in further detail to follow.

Although FIG. 2 illustrates the output data 204 from the tracking device 202 and the ultrasound data output 210 from the ultrasound probe 206 being passed via a tracking interface 220) and an ultrasound sensing interface 222 en route to the input/output of the processing arrangement, this is not essential, and in further examples the data may be passed directly to the processing arrangement 216. For example, the processing arrangement 216 may include local means for treating or processing the raw data from these systems, for subsequent use in the rest of the method.

In either case, the one or more processors 224 are adapted to receive at the input/output 218 the acquired ultrasound data and the acquired tracking data.

The one or more processors 224 of the processing arrangement apply a pre-determined processing operation to the received ultrasound data to derive 228 from each of the ultrasound data samples secondary data relating to features and/or artefacts detectable in each received ultrasound data sample. For example, it may relate to image artefacts detectable in acquired ultrasound image frames.

The pre-determined processing operation may comprise one or more image analysis algorithms including for example shape or pattern detection algorithms, segmentation algorithms, outline detection algorithms, or any other type of image analysis technique. The algorithm may be a machine learning algorithm in certain examples.

The one or more processors 224 are further adapted to process the received tracking data to determine 226 a probe 206 position on the subject body surface as a function of time. This may be represented for example in the form of a vector position of the probe as a function of time. That position may be represented for instance in a co-ordinate system native to the tracking apparatus, or in a co-ordinate system of the anatomical model in some examples. In some examples the two co-ordinate systems may be calibrated one another in an initial step. In some examples, the anatomical model 232 may define a model co-ordinate system 240, and wherein the ultrasound probe 206 position is determined relative to the model co-ordinate system 240.

The one or more processors 224 are further adapted to access an anatomical model 232. This may for example be stored in a local data store 230 comprised by the processing arrangement 216. In further examples it may be stored in a remote datastore to which the processing arrangement is adapted to communicate to retrieve the model, for example via a network or Internet connection which may be wired or wireless. The retrieved anatomical model includes a representation of the anatomical object of interest 212 and of a surface 214 of the subject 208 body overlying the anatomical object of interest, and of a spatial relationship between the anatomical object and the surface 214 of the subject body. The model preferably includes a plurality of subject body surface visual landmarks. As will be explained further below, the model can be a generic model or may be a model personalized to the anatomy of the subject.

The one or more processors 224 are further adapted to generate 234 a surface map representative of a projection of the secondary data values onto a modelled surface of the anatomical object, the projection based on the probe position as a function of time, and based on the anatomical model 232.

By way of example, generating 234 the surface map may be performed in real time with the ultrasound data 210 acquisition and with the determination of the probe position. The one or more processors may further generate in real time a visual representation of the surface map, comprising a visual projection of the secondary data onto a surface of the modelled anatomical object. The real-time generated surface map may be displayed on a display device 236 so that an operator can observe progress of the examination.

The generating of the map may be achieved using a pre-determined algorithm or processing operation. This may for instance include a mapping function which permits mapping of determined body-surface location tags of an acquired set of secondary data samples to a corresponding set of anatomical object surface location tags, this resulting in an effective 2D spatial map of the secondary data values across the modelled surface of the anatomical object.

It is noted that although in the above-described example, the generating of the surface map was performed in real time with acquisition of the tracking data and ultrasound sensing data, in other examples, the tracking data and ultrasound data streams acquired during an examination period might be stored or cached in a local or remote datastore for later retrieval by the processing arrangement. Thus the method may either be performed in real-time with the acquisition of the tracking and ultrasound data or it can be performed 'off-line' based on previously acquired data which is received from a datastore.

Furthermore, although in the above-described example, the generated surface map is output to a display device, this is not essential. In further examples, the generated surface map data may be communicated to a local or remote datastore or memory for storage. For example it may be stored in a database, where the database is recorded or stored in the local or remote datastore. The storage in a datastore may either be done instead of outputting the surface map to a display or in addition to outputting the surface map to the display. For example, if an operator performing the scan is inexperienced, he or she might not themselves need to look at the surface map on a display, since the interpretation may be done by an expert offline at a later time. The system may include a communication interface permitting data communication with a local or remote datastore for storage of the generated surface map. Alternatively, the system may include a datastore for storage of the generated surface map.

Figure 3:
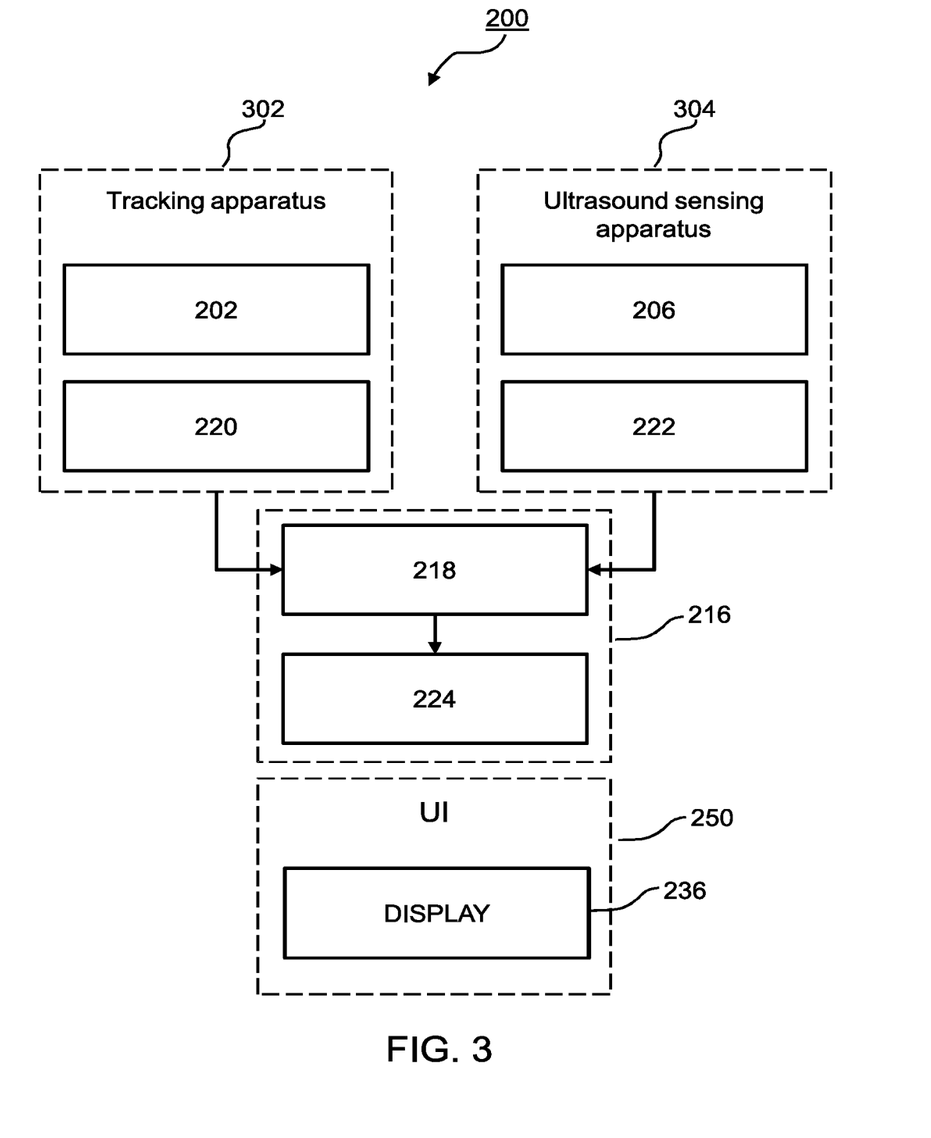
FIG. 3 is a schematic representation of a system for ultrasound imaging of a subject, according to one or more embodiments of the invention.

Referring to FIG. 3, there is depicted a further representation, in block diagram form, of the example system 200 comprising a tracking apparatus 302, an ultrasound sensing apparatus 304, and the previously described processing arrangement 216. The input/output 218 of the processing arrangement 216 is adapted in use to communicatively couple with the tracking apparatus 302 and the ultrasound sensing apparatus 304.

The tracking apparatus 302 may include the tracking device 202 for acquiring tracking data 204 of the ultrasound probe 206 during the course of the examination period and the tracking interface 220. The tracking interface 220) may include in some embodiments a tracking processor arranged to receive the sensing data from the tracking device 202, e.g. camera image data 204, and adapted to output a co-ordinate position of the probe 206 within for instance a camera field-of-view (FOV) 238 co-ordinate system as a function of time.

The ultrasound sensing apparatus 304 includes an ultrasound probe 206 for acquiring ultrasound data during the examination period and an ultrasound sensing interface 222.

In some examples, the system 200 may further comprise a user interface 250 which includes a display 236 for displaying a visual representation of the generated surface map 234. It may additionally or alternatively be controlled to display the tracking data acquired by the tracking apparatus 302, for example the camera image data. It may additionally or alternatively be controlled to display the acquired ultrasound data stream (e.g. live ultrasound images).

Optionally the user interface 250 may include user input means. For example, the user interface 250) may be configured to comprise a touch sensitive screen for use with a stylus or with contact from the user of the interface 236. The user input means may be adapted to permit annotation by a user of locations of one or more visual surface landmarks on a body surface of the user, as depicted in camera images of the body which may be displayed on the display 236 screen. This input may be used as part of registering the tracking system co-ordinate system with a model co-ordinate system, or for personalizing or fitting the model to the anatomy of the subject as will be described further below.

As discussed, the method involves determining a position of the probe on the body surface and relating this position, by means of an anatomical model, to an anatomical object beneath the surface to generate the surface map of secondary data values. One particular approach to achieving this, employing use of a camera, will now be described.

In this example, the tracking device 202 is a camera. The output of the camera is camera image data representative of the field of view 238 including the ultrasound probe 206. Based on this data, a positon of the probe as a function of time on the body surface is required.

A wide variety of computer vision methods exist for tracking the positioning of objects within camera image data, and the skilled person will be aware of suitable means.

By way of example, one method is SLAM (Simultaneous Localization and Mapping). By initially analyzing the environment from different camera positions. SLAM algorithms can create a 3D map and/or model of the environment, with an associated co-ordinate system. This can be used both for tracking the camera position relative to the mapped environment, and also for tracking the position of objects imaged in the camera field of view. The mapped environment may include a 3D map of the body surface of the subject for example. This could be achieved by performing a preliminary initialization or setup routine, in which the subject is imaged using the camera from multiple angles to create the 3D SLAM map, subsequent to which the camera is either placed in a fixed position or is held by hand (e.g. in the case of the camera being a camera of a mobile computing device). The movement of the probe can be tracked in real time within the co-ordinate system of the 3D map, as can any movement of the camera position relative to the probe.

The initial calibration or setup of the SLAM map may in some cases further comprise a step of receiving an indication of a position of the camera relative to the subject at each of the different initial imaging positons. It may further comprise receiving an indication of a position of one or more visual surface landmarks on the body surface of the subject, e.g. by means of a user pointing to the positions on a touch-screen presentation of captured image data. This may assist in calibrating the 3D map to the space being imaged. The surface landmarks may in advantageous examples be the same surface landmarks as are utilized by the anatomical model, as will be discussed below.

More details relating to the implementation of a SLAM method may be found in the review paper: C. Cadena et al., "Past. Present, and Future of Simultaneous Localization and Mapping: Toward the Robust-Perception Age." IEEE TRANSACTIONS ON ROBOTICS, vol. 32, no. 6, p. 24, 2016.

Reference is also made to the following web page, which also provides implementation details for SLAM methods: https://en.wikipedia.org/wiki/Simultaneous_localization_and_mapping.

The above represents just one example of a computer vision algorithm suitable for tracking the positioning of an object within a camera field of view, and the skilled person will be aware of other methods for implementing this technical feature.

A tracking processor might be provided, as previously discussed, and arranged to receive the camera image data and adapted to output a position co-ordinate of the probe within a camera field-of-view (FOV) co-ordinate system as a function of time.

In order to ultimately project the secondary data values onto the modelled anatomical object surface, it may be necessary for the positioning data of the probe as a function of time to be spatially registered or calibrated with a co-ordinate system of the anatomical model. Thus, the resulting position co-ordinates of the probe may need to be transformed into co-ordinates within the co-ordinate system of the subject body, i.e, the co-ordinate system of the anatomical model. This may be achieved using a pre-calibration step between the camera co-ordinate system and the model co-ordinate system.

The pre-calibration may be used to generate a transfer or transposition function by which the tracking interface 220 subsequently converts in real time the co-ordinates of the probe in the camera tracking co-ordinate system into a co-ordinate system of the anatomical model. In a further approach, the two co-ordinate systems may be brought into registration or alignment in a calibration phase so that the tracking co-ordinate system and the model co-ordinate system are effectively the same.

In either case, the registration may be performed in some examples based on registering pre-determined body surface landmarks detectable in the camera image data with subject body surface landmarks in the anatomical model 232. This provides a mechanism for directly registering the native co-ordinate system of the camera image tracking system with the anatomical model co-ordinate system. For example, this may be performed via an initial calibration step wherein the user is guided to position the probe at various pre-defined landmark positions on the body surface. The tracking system co-ordinates for the probe at these known locations can then be registered or aligned or calibrated with the anatomical model co-ordinates for these body surface positions.

Surface visual landmarks in the usage case of lung ultrasound may include, but are not limited to: nipples; axillae; suprasternal notch; and/or xiphoid process. Surface visual landmarks of the subject's chest may be detected automatically and annotated in the camera image by means of image processing techniques. In the case that an automatic landmark detection fails, the system may permit an operator to manually annotate the anatomical landmarks on a still image. The annotations together with a 3D map of the chest embodied in the camera tracking system allow calculating 3D positions of the landmarks. Thus, the method may comprise processing the camera image data to automatically detect the surface landmarks and/or may comprise receiving user input data indicative of a user-indicated position of one or more of the surface landmarks on one or more image frames of the camera image data.

In some specific examples, the method 100 may further comprise a step of receiving an indication of a position of the tracking device 202 relative to the subject 208. This may enable determination of a spatial relation between the co-ordinate system of the tracking data used to determine the probe position, and co-ordinate system of the subject anatomical model.

As mentioned above, in one or more advantageous embodiments, the method can be applied for lung imaging, and wherein the derived secondary data may comprise a representation of the presence of one or more of: lung sliding artefacts. A-line artefacts, and B-line artefacts.

Lung sliding may be recognized by the shimmering of the pleural line with respiration. It is characteristic of the movement of visceral and parietal pleura relative to each other and is thus a sign that visceral and parietal pleura touch each other and that the lung is functioning.

A-line artefacts may be recognized as horizontal reverberation artefacts that occur due to reflection of the ultrasound beam at the pleura. They indicate the presence of air both in healthy lungs as well as in pneumothorax.

B-line artefacts may be recognized as vertical reverberation artefacts appearing as bright vertical lines emerging from the pleura and extending to the bottom of the screen. While B-lines can be found in normal lungs, an increased amount of B-lines are a sign of interstitial fluid and/or pulmonary edema, and can indicate pneumonia. One metric which is particularly pertinent to COVID-19 is counting of B-lines in ultrasound frames. The number of B-lines can be used for monitoring patient status and disease progression over time.

Figure 4:
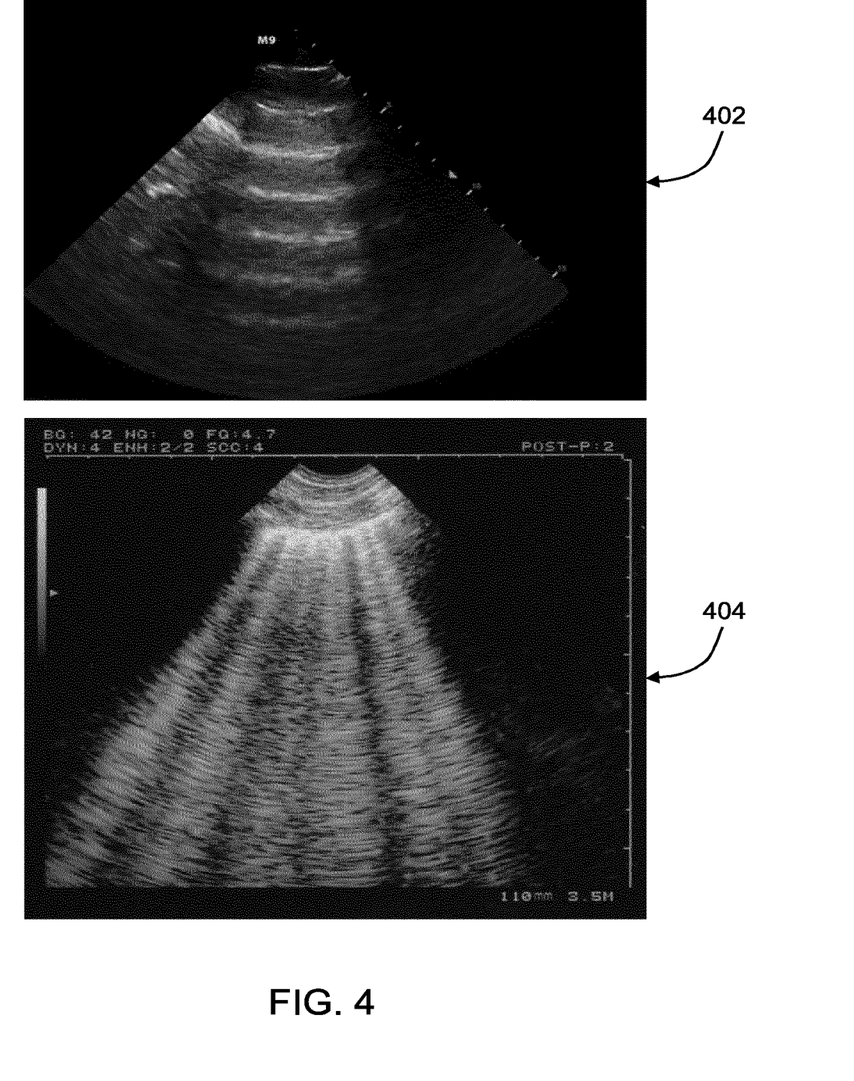
FIG. 4 depicts an example of secondary ultrasound data, according to one or more embodiments of the invention.

Referring to FIG. 4, there is depicted example B-mode ultrasound image frames of the lungs of a subject. Frame 402 in FIG. 4 shows example A-line artefacts in an image of the lungs. Frame 404 shows example B-line artefacts in an image of the lungs.

Image artefacts such as A-line artefacts or B-line artefacts do not carry any 3D information and thus may be mapped on a model of the pleura or of the 2D lung surface without loss of information.

Figure 5:
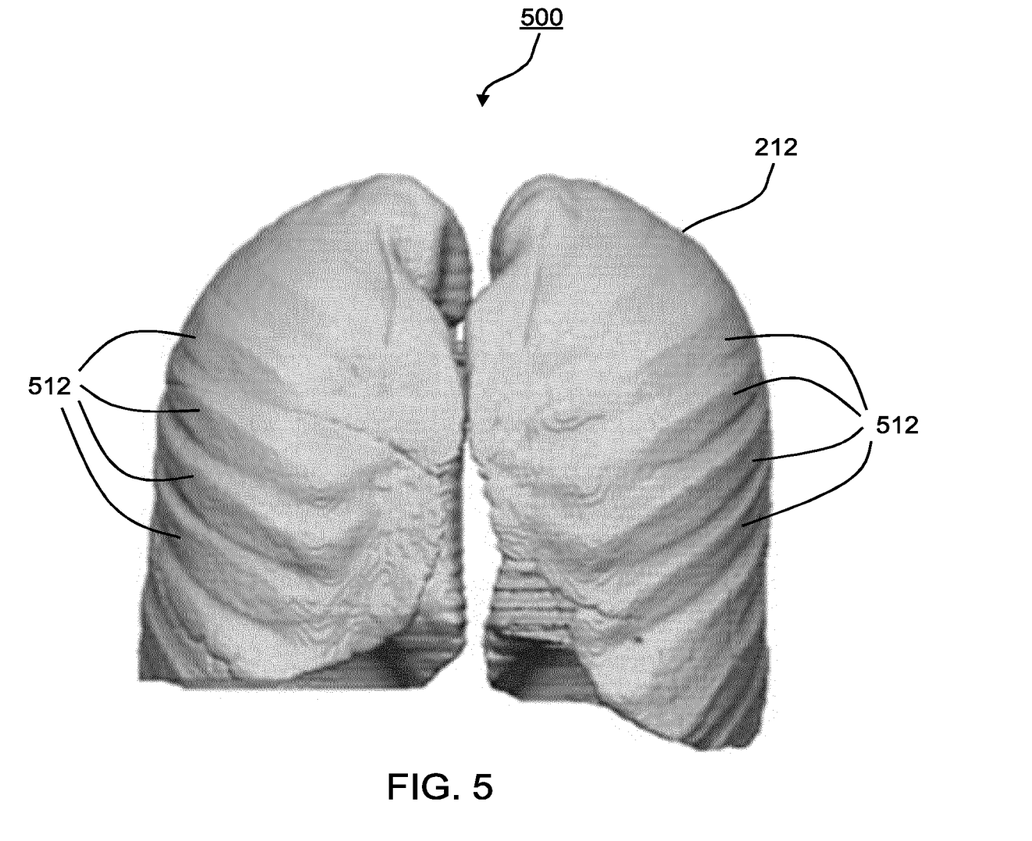
FIG. 5 is an example of a generated visual representation of a surface map projected on to a modelled surface of lungs according to one or more embodiments of the invention.

By way of illustration in FIG. 5, there is depicted a greyscale version of an example visual representation of a surface map 500 generated in accordance with an embodiment. In this example, the anatomical object of interest 212 is the lungs, and the secondary data which is represented by the surface map is the number of B-lines present in ultrasound image frames captured of the lungs at different positions.

Here the derived secondary values have been projected onto a modelled surface of the anatomical object with greyscale values indicative of the magnitude of the derived secondary values. For example, the derived secondary data values can be assigned greyscale values between and including 0 and 255, where 0 indicates black and 255 indicates white. For example, the greatest secondary data value may be assigned the greatest or smallest greyscale value desired and, in a complementary manner, the smallest secondary data value may be assigned the greatest or smallest greyscale value desired. The areas of projected secondary data are the darker shaded areas 512 indicated in the figure.

In further examples, the generated surface map may be a color surface map, and wherein different colors represent different magnitudes of one or more secondary parameters. Alternatively, different colors may represent different secondary parameters, wherein the intensity or transparency of the color represents the magnitude of the secondary data value.

In general, generating the surface map may comprise temporally registering the probe position data with the acquired secondary data, so that each secondary data point has an associated probe position. If the positioning data co-ordinate system or reference frame is registered to that of the anatomical model (as described above), then each secondary data point can be assigned a co-ordinate probe position within the anatomical model co-ordinate system. Generating the surface map may then simply comprise a mapping or projection operation so as to map the body surface locations for each of the secondary data points to a corresponding anatomical object surface location. This may comprise a spatial projection of each value in a direction downward beneath the body surface to the anatomical object surface. In this way, each secondary data point can be assigned a co-ordinate location on the anatomical object surface within the 3D model.

In some examples, interpolation may be performed in case the secondary data does not cover all points across the surface of the anatomical object. However, this is not essential.

The method may comprise creating one or multiple surface maps of the secondary data.

By way of example, for the application case of imaging of the lungs, there may be generated a plurality of surface maps of a modelled surface of the lungs, each comprising a projection of one or more types of ultrasound image feature or artefact atop the modelled lung surface. Each surface map may include a representation or projection of one or more of: information on the presence of A-lines (e.g. binary, logical, and/or yes/no information): the number of B-lines in a frame: the presence of lung sliding (e.g. binary, logical, and/or yes/no information): and/or any other information that may be derived from the secondary data.

Each separate surface map may in some examples be displayed in a single visual representation, for instance by using visually distinct indicators or markers for each secondary data type (e.g. color coding). Alternatively, multiple maps may be shown side-by-side. In some embodiments, the surface maps can be created in real time with the data acquisition. i.e. built up step-by-step during the examination. In some embodiments, the surface maps may be created offline based on previously recorded data, after the examination is completely finished.

As discussed above, embodiments employ use of an anatomical model 232, the model including a representation of the anatomical object of interest and of a surface of the subject body overlying the anatomical object of interest, and of a spatial relationship between the anatomical object and the surface of the subject body. The model may comprise a 3D spatial representation of the shape and structure of at least an outer surface of the anatomical object and the spatial relation between the anatomical object and the body surface.

In some examples, the anatomical model may be a generic model of the anatomical object which has been pre-generated. By generic is meant a population-based model. i.e. a model that is based on an average anatomy, and not personalized to the anatomy of the specific subject being examined. In alternative examples, the anatomical model may be a personalized anatomical model, meaning that it is personalized to the particular geometry of the anatomy of the subject in question.

A personalized anatomical model 232 may be created, by way of example, using software, e.g. a statistical shape model, and wherein software model parameters are adapted in order to create an anatomical model 232 which optimally fits to the measurements of the subject. For example, parameters may be adapted to fit to automatically or manually detected surface visual landmarks on the body surface of the subject. These may be the same or different surface visual landmarks as are optionally used in calibrating or registering the tracking apparatus co-ordinate system.

The method 100 may comprise a step of personalizing an anatomical model 232 for the subject, the personalizing comprising fitting one or more adjustable fitting parameters of the model to the subject based on acquired camera image data of the subject, ultrasound data of the subject, and/or measurement or personal characteristics data of the subject. The measurement data may include standard measurements of the subject, e.g. height, weight, chest and waist circumference. Personal characteristics data may include for example age, gender, ethnicity, relevant medical history.

This step may be done in real time with the acquisition of the ultrasound data and/or tracking data in some examples. Alternatively, it may be done in a preliminary setup phase before the main method begins.

Where the tracking data 204 is camera image data, the fitting of the anatomical model may be based on identifying one or more body surface visual landmarks comprised by the model in the one or more camera image frames: and fitting the parameters of the initial model to the subject body surface based on the landmarks to derive the personalized subject model.

The personalization of the anatomical model may be performed in a preliminary setup phase of the method, the setup phase performed for example in advance of receiving the ultrasound data. The setup phase may comprise: retrieving an initial version of the anatomical model, and wherein the model includes a plurality of adjustable fitting parameters: acquiring one or more camera image frames of the subject body surface 214: identifying the one or more surface landmarks in the one or more camera image frames: and fitting the parameters of the initial model to the subject body surface 214 based on the landmarks to derive the personalized subject model. In this set of embodiments, the personalizing of the anatomical model is done as a preliminary step of the method. The initial version of the model may for example be a generic population-based model, using average values for the anatomy structure and dimensions.

Additionally or alternatively, the model may be personalized to the subject in advance of the method beginning, based on personal medical image data for the subject, e.g. based on computed tomography (CT) medical image data, e.g. x-ray CT scan data. It may further be personalized based on non-image medical data for the subject such as height, weight, age, gender. In this way, once the method 100 starts, the accessed anatomical model 232 is already personalized to the subject anatomy.

By way of example, reference is made to the following paper which describes a method for generating a personalized anatomical model based on CT image data: Thomas Blaffert, et al, "Lung lobe modeling and segmentation with individualized surface meshes." Proc. SPIE 6914. Medical Imaging 2008: Image Processing. 691411 (11 Mar. 2008).

In some examples, the personalizing of the model may be done in real time. i.e. on the fly, during the acquisition of the ultrasound data and position tracking data. The personalization may be recurrently updated throughout the acquisition of the ultrasound and tracking data. In this way, the model parameter fitting can be recurrently or continuously updated or adjusted as the data acquisition progresses based on the data being acquired. In advantageous examples, the model fitting may be performed in part based on the acquired ultrasound data of the anatomical object. In this way, not only the body surface parts of the model, but also the internal anatomical areas of the model, can be optimally personalized to the anatomy of the subject.

In accordance with one or more embodiments, the method may comprise generating and outputting user guidance information for guiding a user in positioning the ultrasound probe in an appropriate set of predetermined positions for acquiring the ultrasound data. For example, the method may comprise accessing a predetermined scan protocol including a series of target positions for the ultrasound scanner during the examination period, and generating a display output for presentation on a display device 236 representative of the target probe positions of the scan protocol superimposed upon an image representation of the subject body surface 214. The image representation may be provided by real time camera image data in the case that the tracking data 204 is camera image data, or may be a graphical representation of the body surface, e.g. a model representation of the body surface.

The anatomical model 232 may contain the predetermined scan protocol for scanning the anatomical object. i.e. positions where images should be taken. The scan protocol may be registered to the personalized anatomical model 232 of the subject 208 and to the camera tracking system, such that geometrical information indicating where an ultrasound probe should be positioned can be overlaid onto the live camera stream. In the case that the user of the method and/or system does not require assistance and/or is experienced, this overlay may be omitted. In some examples for instance, the guidance function described above may be selectively activated or deactivated.

In the case that the user of the method 100 and/or system requires assistance and/or is not experienced, the user is enabled to begin scanning by following the on-screen instructions for carrying out the scan protocol. The instructions and/or scan protocol may be determined since the ultrasound probe 206 is visible in the camera image. Since the location and geometry of the ultrasound probe 206 is known, the software is able to track the 3D position and orientation of the ultrasound probe 206 relative to the subject body surface in the subject co-ordinate system. The software may guide the user in scanning with the ultrasound probe 206 at the right positions and the software may give hints if the user deviates from the predefined scanning protocol. The ultrasound image stream 210 and the stream of probe positions (in the subject co-ordinate system) are recorded synchronously. It is thus known from which position each ultrasound frame is captured. This allows inexperienced users to perform the ultrasound examination at the point-of-care. If performed in real-time, this display output effectively provides an augmented reality image representation of the subject body surface, augmented with the target probe positions.

Embodiments of the invention described above employ a processing arrangement. The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented. The processing arrangement includes a communication module or input/output for receiving data and outputting data to further components. In some examples, the processing arrangement may be local to the tracking apparatus and ultrasound imaging apparatus or it may be physically remote from these systems, for instance implemented by a remote computer or server, or for instance implemented by a cloud-based processing system.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM. PROM. EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A computer-implemented method for use in ultrasound examination of an internal anatomical object of a subject, comprising:
   receiving ultrasound data comprising a series of data samples acquired from an ultrasound probe moved over a surface of a body of the subject during a first period;
   applying a pre-determined processing operation to derive from the ultrasound data samples secondary data relating to features and/or artefacts detectable in at least a subset of the ultrasound data samples;
   receiving tracking data representative of movement of the ultrasound probe over the body surface during the course of the examination period;
   accessing an anatomical model, the model including a representation of (i) the anatomical object of interest and (ii) a surface of the body overlying the anatomical object of interest, and (iii) a spatial relationship between the anatomical object and the surface of the body;
   determining, based on the tracking data, a probe position on the body surface as a function of time; and
   generating a surface map comprising a projection of the secondary data values onto a surface of the anatomical object, the projection based on the probe position as a function of time, and based on the anatomical model.

2. A method as claimed in claim 1, wherein:
   the tracking data is camera image data representative of the movement of the probe over the body surface.

3. A method as claimed in claim 1, further comprising generating a visual representation of the surface map, comprising a visual projection of the secondary data onto the surface of the modelled anatomical object.

4. A method as claimed in claim 1, wherein the ultrasound data samples are ultrasound image frames, and the secondary data relates to presence of pre-determined types of image features and/or image artefacts within each image frame.

5. A method as claimed in claim 1, wherein the ultrasound data is received in real time with the data acquisition by the probe, and wherein the receiving the tracking data and the determining the probe position is performed in real time with the receipt of the ultrasound data.

6. A method as claimed in claim 5, wherein the generating of the surface map is performed in real time with the ultrasound data acquisition and with the determination of the probe position, and optionally wherein the method further comprises generating in real time a visual representation of the surface map, comprising a visual projection of the secondary data onto a surface of the modelled anatomical object.

7. A method as claimed in claim 1, wherein the method further comprises accessing a predetermined scan protocol including a series of target positions for the ultrasound scanner during the examination period, and generating a display output for presentation on a display device representative of the target probe positions of the scan protocol superimposed upon an image representation of the subject body surface.

8. A method as claimed in any claim 1, wherein the method comprises a step of personalizing the accessed anatomical model for the subject, the personalizing comprising fitting one or more adjustable fitting parameters of the model to the subject based on acquired camera image data of the subject, ultrasound data of the subject, and/or measurement data of the subject.

9. A method as claimed in claim 2, wherein the anatomical model is a personalized anatomical model for the subject, and wherein the method further comprises a preliminary setup phase for configuring the personalized anatomical model, the setup phase performed in advance of receiving the ultrasound data, and comprising:

retrieving an initial version of the anatomical model, and wherein the model includes a plurality of adjustable fitting parameters, and the model comprising one or more body surface visual landmarks;

acquiring one or more camera image frames of the subject body surface;

identifying the one or more body surface visual landmarks in the one or more camera image frames; and fitting the parameters of the initial model to the subject body surface based on the landmarks to derive the personalized subject model.

10. A method as claimed in claim 9, wherein the method comprises processing the camera image data to automatically detect the surface landmarks; and/or wherein the method comprises receiving user input data indicative of a user-indicated position of one or more of the surface landmarks on one or more image frames of the camera image data.

11. A method as claimed in claim 1, wherein the anatomical object of interest is the lungs, and wherein the secondary data comprises a representation of presence of one or more of: lung sliding artefacts, A-line artefacts, and B-line artefacts.

12. A computer program product comprising code means configured, when executed on a processor, to cause the processor to perform a method in accordance with claim 1.

13. A processing arrangement comprising:

an input/output; and one or more processors adapted to:

receive at the input/output ultrasound data comprising a series of data samples acquired from an ultrasound probe moved over a surface of a body of a subject during an examination period;

apply a pre-determined processing operation to derive from the ultrasound data samples secondary data relating to features and/or artefacts detectable in at least a subset of the ultrasound data samples;

receive at the input/output tracking data representative of the movement of the ultrasound probe over the body surface during the course of the examination period;

access an anatomical model, the model including a representation of (i) the anatomical object of interest and (ii) a surface of the body overlying the anatomical object of interest, and (iii) a spatial relationship between the anatomical object and the surface of the body;

determine, based on the tracking data, a probe position on the subject body surface as a function of time; and generate a surface map representative of a projection of the secondary data values onto a surface of the anatomical object, the projection based on the probe position as a function of time, and based on the anatomical model.

14. A system, comprising:

an ultrasound sensing apparatus including an ultrasound probe for acquiring ultrasound data;

a tracking apparatus for acquiring tracking data of the ultrasound probe during the course of the examination period; and a processing arrangement as claimed in claim 13, the input/output of the processing arrangement communicatively coupled with the tracking apparatus and the ultrasound sensing apparatus for receiving the tracking data and the ultrasound data respectively.

15. A system as claimed in claim 14 further comprising a user interface for displaying a visual representation of the generated surface map, and optionally wherein the user interface is further adapted to permit annotation by a user of locations of one or more surface visual landmarks in each of one or more image frames from the camera image data.

* * * * *